(12) United States Patent
Biffinger et al.

(10) Patent No.: US 8,969,635 B2
(45) Date of Patent: Mar. 3, 2015

(54) ALKANE ENHANCEMENT OF WASTE USING MICROBIAL PRE-TREATEMENT

(75) Inventors: Justin C. Biffinger, Woodbridge, VA (US); Lisa A. Fitzgerald, Alexandria, VA (US); Cherie Ziemer, Ames, IA (US); Kurt Henry, Arlington, VA (US); Bradley R Ringeisen, Lorton, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 880 days.

(21) Appl. No.: 12/913,169

(22) Filed: Oct. 27, 2010

(65) Prior Publication Data

US 2011/0098520 A1  Apr. 28, 2011

Related U.S. Application Data

(60) Provisional application No. 61/255,169, filed on Oct. 27, 2009.

(51) Int. Cl.
*C10L 1/16* (2006.01)
*C12P 7/64* (2006.01)
(Continued)

(52) U.S. Cl.
CPC ........... *C12P 7/6409* (2013.01); *C10G 1/02* (2013.01); *C10G 3/40* (2013.01); *C10G 21/00* (2013.01); *C10G 2300/1011* (2013.01); *C10G 2300/1018* (2013.01); *C12P 5/02* (2013.01)
USPC ............ 585/14; 585/240; 585/469; 585/638; 585/733; 44/307; 44/605

(58) Field of Classification Search
CPC ............... C10L 1/00; C10L 1/14; C10L 1/16; C10M 101/02; C10M 107/20; C10M 107/22; C10M 107/26; C10M 107/28; C07C 1/20; C07C 1/207; C07C 1/213
USPC ............. 44/307, 605; 585/14, 240, 469, 638, 585/733; 208/113–124
See application file for complete search history.

(56) References Cited

U.S. PATENT DOCUMENTS 4,018,671 A * 4/1977 Andon et al. ............... 208/152
4,891,130 A * 1/1990 Pitts ............................ 208/305

(Continued)

FOREIGN PATENT DOCUMENTS

| WO | 2009006430 A1 | 1/2009 |
| WO | 2009073816 A1 | 6/2009 |
| WO | 2009083174 A1 | 7/2009 |

OTHER PUBLICATIONS

Dunlap, R.H. et al. (1998) Applied and Environmental Microbiology, 64(1), 366-369.*

(Continued)

*Primary Examiner* — Brian McCaig
(74) *Attorney, Agent, or Firm* — US Naval Research Laboratory; Joseph T. Grunkemeyer (57) ABSTRACT

A method of: providing a mixture of fecal waste and a bacterium; incubating the mixture to produce a fatty acid enriched mixture; removing water from the fatty acid enriched mixture to produce a dried mixture; and pyrolyzing the dried mixture in an inert atmosphere to produce an alkane from the $C_5$-$C_{32}$ fatty acid. The bacterium is a type that produces a $C_5$-$C_{32}$ fatty acid in the presence of any microbes in the fecal waste.

17 Claims, 11 Drawing Sheets

(51) Int. Cl.
*C10G 1/02* (2006.01)
*C10G 3/00* (2006.01)
*C10G 21/00* (2006.01)
*C12P 5/02* (2006.01)
*C07C 1/20* (2006.01)
*C07C 1/207* (2006.01)
*C07C 1/213* (2006.01)
*C10L 1/00* (2006.01)
*C10L 1/14* (2006.01)
*C10M 101/02* (2006.01)

(56) References Cited

U.S. PATENT DOCUMENTS

| | | | |
|---|---|---|---|
| 6,830,597 | B1 | 12/2004 | Green |
| 2004/0254068 | A1* | 12/2004 | Fung et al. ............ 502/208 |
| 2008/0293607 | A1* | 11/2008 | Jones et al. ............ 510/226 |
| 2009/0017513 | A1 | 1/2009 | Bell et al. |
| 2009/0047721 | A1* | 2/2009 | Trimbur et al. ............ 435/167 |
| 2009/0069610 | A1 | 3/2009 | Roberts, IV et al. |
| 2009/0121798 | A1 | 5/2009 | Levinson |
| 2009/0139134 | A1 | 6/2009 | Yoshikuni et al. |
| 2009/0181438 | A1 | 7/2009 | Sayre |
| 2010/0170148 | A1 | 7/2010 | Steen et al. |
| 2012/0108841 | A1* | 5/2012 | Tenedorio Matos Da Silva et al. ............ 560/179 |

OTHER PUBLICATIONS

Gary, J.H. (2007). Petroleum Refining Technology and Economics, 5$^{th}$ ed, CRC Press, 465 pgs [Office action references definition of "dry gas" on p. 391].*
Rude et al., "New microbial fuels: a biotech perspective" Current Opinion in Microbiology, 12, 274-281 (2009).
Shirmer et al., "Microbial Biosynthesis of Alkanes" Science, 329, 559-562 (2010).
Steen et al., "Microbial production of fatty-acid-derived fuels and chemicals from plant biomass" Nature, 463, 559-563 (2010).

* cited by examiner

ALKANE ENHANCEMENT OF WASTE USING MICROBIAL PRE-TREATEMENT

This application claims the benefit of U.S. Provisional Application No., 61/255,169 filed on Oct. 27, 2010. The provisional application and all other publications and patent documents referred to throughout this nonprovisional application are incorporated herein by reference.

TECHNICAL FIELD

The present disclosure is generally related to the formation of hydrocarbon fuels from fecal waste.

DESCRIPTION OF RELATED ART

With the rising cost of oil and the need to lower carbon emissions, large consumers of fuel may seek to rely more heavily upon alternative pathways to produce aviation fuels in the coming years. Military installations and ships, for example, produce large quantities and diverse types of waste (human, grey water, bilge water, oil/lubricants, etc.) (Singerman et al. "Survey of Technologies to Treat the Shipboard Incidental Liquid Wastes Identified During the Process to Set Uniform National Discharge Standards" (Navy, U., Ed.) CDNSWC-TR-63-CR-98/29 ed., Naval Surface Warfare Center (2000)).

The microbial ecology of human and animal wastes is complex with high diversity of bacterial species and metabolic capabilities (Kerr et al., "Manure composition of swine as affected by dietary protein and cellulose concentrations" *J. Anim. Sci.*, 84, 1584-1592 (2006); Updegraff, "Microbiological aspects of solid-waste composting" *Develop. Ind. Microbiol.*, 13, 16-23 (1972)). Research into the generation of energy from these wastes has primarily focused on gas generation (especially methane and hydrogen) (Dietenberger et al. "Vision of the U.S. Biofuel Future: A Case for Hydrogen-Enriched Biomass Gasification" *Ind. Eng. Chem. Res.*, 46, 8863-8874 (2007); Lee, "Energy from biomass conversion" *Handb. Altern. Fuel Technol.*, 377-393 (2007)). While there is some work focused on ethanol and biodiesel production from wastes (fuels used for ground transportation primarily), little effort has focused on long chain hydrocarbon production for aviation fuel (Dagaut et al., "Chemical Kinetic Study of the Effect of a Biofuel Additive on Jet-A1 Combustion" *J. Phys. Chem. A*, 111, 3992-4000 (2007)). Biomass conversion to aviation fuel has gained attention recently by the production of so-called "biokerosene", which is generated via a multi-step process requiring intense external energy input (gasification of the biomass with subsequent condensation via Fischer-Tropsch (FT) process) (Lamprecht, "Fischer-Tropsch Fuel for Use by the U.S. Military as Battlefield-Use Fuel of the Future" *Energy Fuels*, 21, 1448-1453 (2007)).

One hurdle to directly convert waste and biomass into aviation fuel is that the primary fuel components are long-chain alkanes with lengths between ten to twenty carbons. Specifically, Navy-relevant JP-5 is kerosene-based with a distribution of alkanes ranging between $C_{10}$-$C_{19}$ in carbon length with residual polyaromatic hydrocarbons (Shepherd et al., "Flash Point and Chemical Compostion of Aviation Kerosene (Jet A)" (Board, N. T. S., Ed.), California Institute of Technology (2000); Van Winkle et al., "Liquid and solid phase compositions in a partially frozen JP-5 fuel low in n-alkanes" p. 19 pp, Nav. Res. Lab., Washington, D.C. (1984)). The major components of human feces are water (75%) and various solids (25%). Kerosene-like compounds can be obtained from the solid components of human waste by utilizing natural fatty acid from four sources: undigested dietary lipids, host lipids excreted in feces, bacterial membranes and products of bacterial fermentation.

The pyrolysis of human waste with microwaves instead of conventional technologies has found increasing applications in recent years (Menendez et al., "Microwave-induced pyrolysis of sewage sludge" *Water Res.*, 36, 3261-3264 (2002); Wang et al., "The influence of microwave drying on biomass pyrolysis" *Energy Fuels*, 22, 67-74 (2008)). Compared to conventional heating, microwave devices severely reduce heat transfer resistances since the heating occurs at a molecular level and not the chamber wall. Therefore, microwave processing may result in higher heating efficiencies and rates (Mingos et al., "Applications of microwave dielectric heating effects to synthetic problems in chemistry" *Microwave-Enhanced Chem.*, 3-53 (1997)). Microwave pyrolysis may also result in a higher fraction of bio-oils and less coking than conventional heating (Dominguez et al. "Investigations into the characteristics of oils produced from microwave pyrolysis of sewage sludge", *Fuel Process. Technol.*, 86, 1007-1020 (2005)).

BRIEF SUMMARY

Disclosed herein is a method comprising: providing a mixture comprising fecal waste and a bacterium; incubating the mixture to produce a fatty acid enriched mixture; removing water from the fatty acid enriched mixture to produce a dried mixture; and pyrolyzing the dried mixture in an inert atmosphere to produce an alkane from the $C_5$-$C_{32}$ fatty acid. The bacterium is a type that produces a $C_5$-$C_{32}$ fatty acid in the presence of any microbes in the fecal waste.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Figure 1:
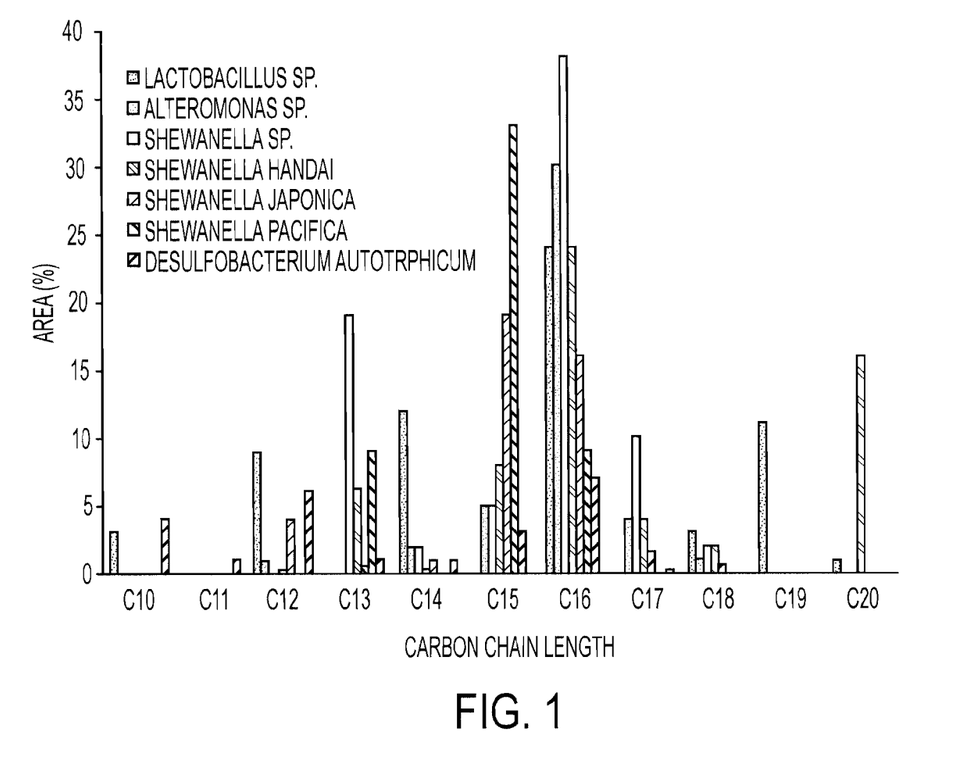
FIG. 1 shows the reported natural fatty acid distribution of certain microbes.

Disclosed herein is a method to create a biocatalyzed, low-input energy approach to convert fecal waste into usable jet fuels (JP-5, JP-8, JP1) and lubricants using microbial pre-treatment and adaptation. A microbial treatment is used to condition the waste such that higher order carbons are synthesized (intracellular, membrane-bound and extracellular) through natural enzymatic metabolic pathways. The applicable microbes may be screened based on their natural fatty acid distributions, to identify those that may produce a distribution of alkanes similar or identical to that of JP-5 (carbon chain lengths between $C_9$-$C_{25}$), or any other desired alkane profile from $C_5$-$C_{32}$. As used herein, "alkanes" can include alkenes and alkynes. FIG. 1 shows the reported natural fatty acid distribution of certain microbes.

In order to obtain kerosene components with a distribution from $C_{10}$-$C_{19}$ for JP-5, waste must be conditioned or pre-treated prior to pyrolysis. Pyrolysis alone will not yield carbon chain lengths relevant to aviation fuel products. Both in vivo (swine model) and ex vivo (batch culture) microbial approaches may be used to catalyze the production of higher order carbon species. Pyrolysis (such as by convection heating or microwaves) is used to efficiently convert the treated waste into kerosene and kerosene-like components.

By combining biocatalysis and pyrolysis, a larger fraction of the waste may be efficiently converted into medium-to-long chain fatty acids (M-LCFA) and subsequently into long chain alkanes. The process completely circumvents the prior pathway to biokerosene (gasification and FT processing) to efficiently produce components of jet fuels directly from waste with minimal energy input.

One practical example of how this method may be utilized would be to convert shipboard waste into potable water, lubricants, and aviation fuel. A US Navy Nimitz class aircraft carrier can hold 114,000 tons of human waste for disposal and 70% of that is water. Due to the high temperatures achieved during pyrolysis, the process could create nearly 18 million gallons of sterile water that could be stored for distribution. This would leave behind 34,000 tons of solid waste precursor for JP-5 processing. The amount of kerosene components directly usable in this solid waste is minimal. However, by microbially treating the waste to enhance M-LCFA components, up to 70% of the solid waste remaining could be converted into JP-5 components through pyrolysis. Additionally, by-products of the pyrolysis include useful materials such as polyaromatic hydrocarbons (aviation fuel components), oils (lubricants), and energy-rich gases ($CO$, $H_2$) that could be used in fuel cells to generate supplemental electricity. Currently, there are four gallons of kerosene-type jet fuel that can be isolated from one barrel of crude oil. The processing of shipboard waste may result in approximately 2 gallons of kerosene type jet fuel from one barrel of biocrude oil.

The method capitalizes on the concept that microbes that generate a natural fatty acid distribution similar to aviation fuel mixtures and lubricants can be utilized to enhance the concentration of aviation fuels and lubricants from biomass derived waste. The results indicate that the use of microbes with the natural fatty acid distribution similar to aviation fuels can be utilized to enhance waste streams for fuel generation. This process is not exclusive to only Shewanella strains, as many other γ, δ, or β proteobacteria would also be suitable as well as Saccharomyces cerevisiae grown under limited oxygen atmospheres.

The method begins with providing a mixture comprising fecal waste and a bacterium. The fecal waste may be from any animal, including but not limited to, human and swine waste. The waste may be from one animal but be a simulant of another animal. For example, with the proper diet, swine waste may a simulant for human waste. The waste may be partially dried before use. The bacterium may be any bacterium that produces a $C_5$-$C_{32}$ fatty acid in the presence of any microbes in the fecal waste. These fatty acids include those containing 5, 6, 7, 8, 9, 10, 11, 12, 13, 14, 15, 16, 17, 18, 19, 20, 21, 22, 23, 24, 25, 26, 27, 28, 29, 30, 31, or 32 carbon atoms. Other microbes in the waste should not prevent the bacterium from producing the fatty acids, and may possibly enhance the production of fatty acids through chemical or physical interactions between the bacterium and the other microbes. It is not a requirement that the other microbes be present in the fecal waste. Suitable bacteria include, but are not limited to, environmental or wild type bacteria; spontaneous genetic mutants, environmentally conditioned strains, and genetically engineered mutants of wild type bacteria; a Shewanella bacteria; Shewanella japonica; Shewanella colwellianna; and Shewanella oneidensis. S. oneidensis may tend to make more $C_9$ and lower alkanes while S. japonica and S. colwellianna may tend to make more $C_9$ and higher alkanes.

Comparative genomic analysis is one approach to identify genes encoding proteins that are involved in the biosynthesis of hydrocarbons. One such identified family of proteins is the Ole proteins, which are proposed to be directly involved in the biosynthesis of hydrocarbons and hydrocarbon intermediates. A proposed olefin biosynthesis pathway (below) utilizes two Ole family proteins (OleA and OleD).

Bacterial hydrocarbon biosynthesis has led to renewed interest in the context of generating biofuels that are superior to ethanol. A number of bacteria make long-chain, non-isoprenoid hydrocarbons which are currently being explored for transportation fuels.

Stenotrophomonas maltophilia OleA and OleD recombinant proteins were used as a basis for a bioinformatic study due to their catalytic activity in vitro. Their sequence homology was compared to Shewanella oneidensis MR-1, the wild-type of the chosen bacterial family. There was a 34 and 48 percent identity between the OleA and OleD proteins, respectively. The occurrence of these two particular proteins from Shewanella oneidensis MR-1 to other organisms was determined. The comparison of OleD proteins from several organisms identified a high percentage of sequence similarity but not as conserved as the OleA proteins. Additionally, *Shewanella oneidensis* MR-1 OleA and OleD proteins were aligned to other *Shewanella* species. The results show high sequence identity between *Shewanella* species. Thus, this proposed metabolic pathway is highly conserved in *Shewanella* sp. and can enhance alkane production from defined waste streams prior to pyrolysis. These methods may be used to identify other microbes suitable for hydrocarbon production.

The mixture may be prepared by any method that produces a suitable mixture of the components so that the bacterium has access to the waste material and any other microbes therein. Other components may also be present in the mixture.

The mixture is incubated so that the bacterium produces fatty acids. Any incubation conditions that result in fatty acid production may be used. The incubation may be performed at or near room temperature and may continue for any amount of time that results in fatty acid production. In some embodiments, the presence of other microbes in the fecal waste may enhance the ability of the bacterium to produce the fatty acids.

After the incubation, water is then removed from the mixture. The water may be removed by, for example, heating the mixture. Optionally, the removed water may be collected and used for other purposes. The water may be sterile and potable.

After removing water, the mixture is pyrollized in an inert atmosphere, such as nitrogen or argon. Water removal and pyrolysis may both be done in the same manner and with a continuous heating profile. Suitable methods of pyrolysis include, but are not limited to, heating in a furnace or oven and microwave irradiation. Small scale microwave pyrolysis may be done, for example, in a 600 W commercial microwave oven in just 1 minute, at a temperature of 650° C. A microwave heating process can be scalable, including ton-scale. Microwave pyrolysis can allow for fast uniform heating, better temperature control, and increased yield of oils and less polyaromatic hydrocarbons than in conventional heating.

Pyrolysis converts at least a portion of the fatty acids to alkanes. Typically, the entire carboxyl group (COOH) is removed from the fatty acid, though other reactions are also possible. The reaction may be catalyzed by components of the fecal waste, such as metals or compounds made by other microbes in the waste. The pyrolysis may also produce a quantity of gases such as CO, $CO_2$, and $H_2$. These gases may also be collected and used for other purposes. The heating rate of the pyrolysis may be any rate that results in production of alkanes. In general, a slower heating ramp may produce a higher fraction of alkanes and a faster ramp may produce a higher fraction of gases.

After pyrolysis, the mixture may contain a relatively high percentage of desired alkanes. These alkanes may be isolated from the pyrolized mixture and used for any suitable purpose including, but not limited to, use as a fuel.

The utility of using defined and conditioned microbial pre-treatments to selectively increase the required paraffin components (Long chain ($C_9$-$C_{20}$) saturated and unsaturated fatty acids) of JP-5 and aviation fuel lubricants within defined fecal waste streams has been demonstrated. In order to bring the invention to practice, facultative anaerobic environmental microbes (*Shewanella oneidensis* MR-1, *Shewanella colwellianna*, and *Shewanella japonica*) were cultured in swine waste for 0, 24, and 48 hours. These microbes are sustainable without light and oxygen and can be conditioned with swine waste to create natural adaptations to environmental stressors found in fecal waste.

The following examples are given to illustrate specific applications. These specific examples are not intended to limit the scope of the disclosure in this application.

EXAMPLE 1

Swine waste collection and sampling—Swine waste was chosen because it is a verified simulant for human fecal waste and its composition can be manipulated directly through diet. Eight pigs were fed a standard corn and soybean meal based diet (balanced to meet their maintenance and growth requirements) at a rate of 3.5 kg/d and housed at the Iowa State Swine Nutrition Farm. Pigs were approximately 80 kg body weight and were housed in metabolism crates (1.2×2.4 m). Pigs were randomly assigned to one of two groups and fecal and urine from the pigs in each group was pooled into a single waste tank. Total feces and urine were collected daily and transferred to waste tanks (stainless steel tanks 122 cm high and 96.5 cm in diameter fitted with a lid that allowed for air exchange). Waste was collected in tanks for 5 weeks. Prior to sampling the contents of a tank was mixed with a paddle. Samples (900 ml) were taken using a sampler (Sludge Judge®, Nasco, Inc., Fort Atkinson, Wis.) on weeks 2, 3, 4 and 5. Samples were immediately frozen at −20° C. Samples were shipped frozen, overnight for analyses.

EXAMPLE 2

Figure 2:
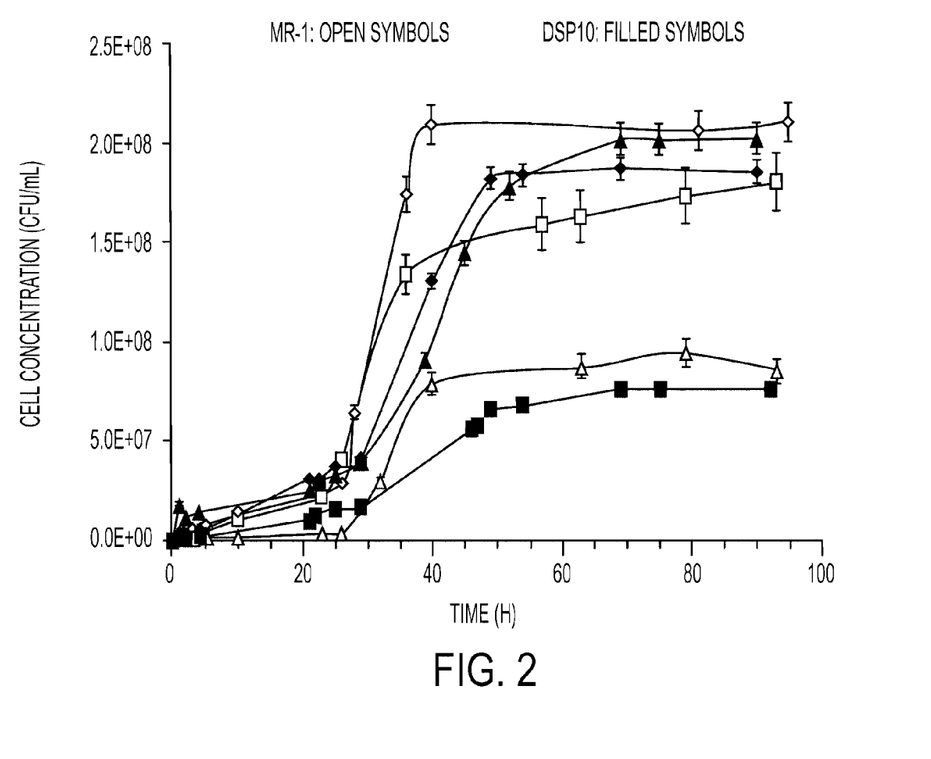
FIG. 2 shows growth characteristics in LB for *S. oneidensis* DSP10 and *S. oneidensis* MR-1 at pH 5, pH 6, and pH 7. Triangles: pH 7, Diamonds: pH 6, Squares: pH 5 (Biffinger, J. C., et al., *Biosens. Bioelectron*, 2008, 24(4), 906-911)
Figure 3:
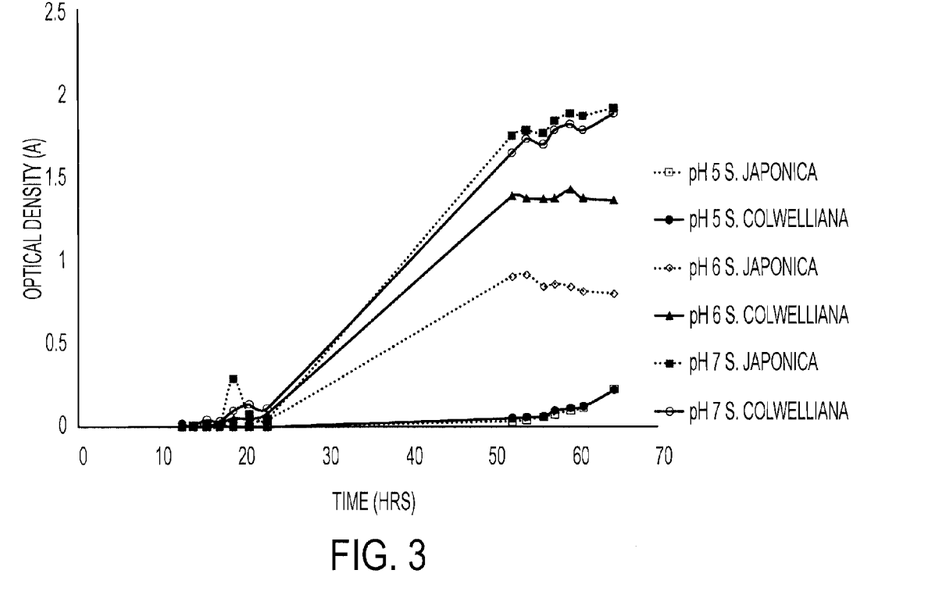
FIG. 3 shows growth of *S. colwellianna* and *S. japonica* in MB at pH 5, pH 6, and pH 7.

Growth of *Shewanella* with variable pH—Acidity is a common environmental stressor utilized to alter protective fatty acid production on the outer membrane of microbes. In addition, the pH of fecal waste is usually between pH 7.4 and 6.2 so pH tolerance is a pre-requisite to utilizing *S. oneidensis* MR-1, *S. japonica*, and *S. colwellianna* in defined waste streams. Standard growth curves were obtained by turbidity measurements using a optical density measurements with standardized turbidity plots for *S. oneidensis* MR-1 and DSP10 at pH 5, 6, 7 (FIG. 2) in Luria-Bertani (LB) broth and *S. colwellianna* and *S. japonica* in marine broth (MB) (FIG. 3) to equate cell count (determined by plating after serial dilution on LB/Agar or MB agar plates at 30° C.) with absorbance. Marine broth is comprised of salt concentrations identical to marine environments where water will ultimately be obtained for an operational full scale device. Error for each cell count measurement was ±1×$10^7$ CFU/mL. The standardization cultures and growth cultures (80 mL each) were all inoculated with 2 mL of a stock culture of bacteria in parallel. The cultures were grown in 125 mL baffled shaker flasks (100 rpm at 25° C.). FIG. 2 shows that the spontaneous mutant of MR-1, DSP10, is not as tolerant to large pH changes. This data also suggests that the spontaneous acid tolerant mutant of MR-1 that is generated from persistent sub-cultures is more acid tolerant than MR-1 initially.

The results for MR-1 are significantly different compared to *S. colwellianna* and *S. japonica* at pH 5, 6, and 7. Results are plotted as optical density for *S. colwellianna* and *S. japonica* normalized to cell count via serial dilution and plating techniques. At pH 7 the two strains grow with similar rates while neither strain grows well at pH 5. These results suggest that the strains of *Shewanella* used for this work are sufficiently amendable to the diverse range of pH conditions encountered in waste treatment. Bioremediation at neutral pH will result in a higher biomass of each microbe (thus higher aviation fuel component) but this benefit might be counterbalanced with the energetic cost to maintain this pH throughout the cycle.

EXAMPLE 3

Figure 4:
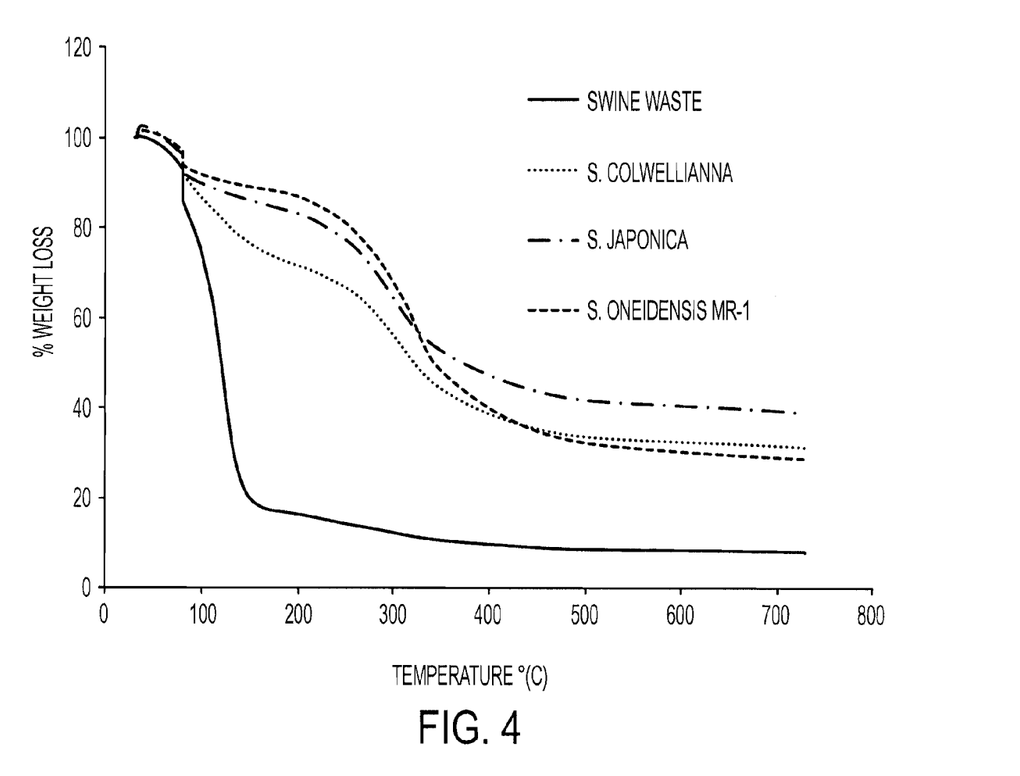
FIG. 4 shows pyrolysis of bulk *S. colwellianna*, *S. japonica*, and *S. oneidensis* MR-1 grown in MB.

Pyrolysis of *Shewanella*—*S. oneidensis* MR-1, *S. colwellianna*, and *S. japonica* samples were prepared from cell pellets after growth in MB. Cell pellets were dried in a vacuum oven (80° C., 33 mm Hg, 15 min) to a constant weight. Cells were then place in 70 μL alumina crucibles heated to 730° C. (30-80° C. (20° C./min), 80° C. for 1 min, 80-730° C. (10° C./min), 730° C. for 5 min) with a full temperature scan TGA/DSC method. Results for each bacterium are shown in FIG. 4 versus swine waste with the same protocol. These data indicate that *S. oneidensis* has the highest percentage of pyrolysis content (>13%) compared to swine waste.

EXAMPLE 4

Figure 5:
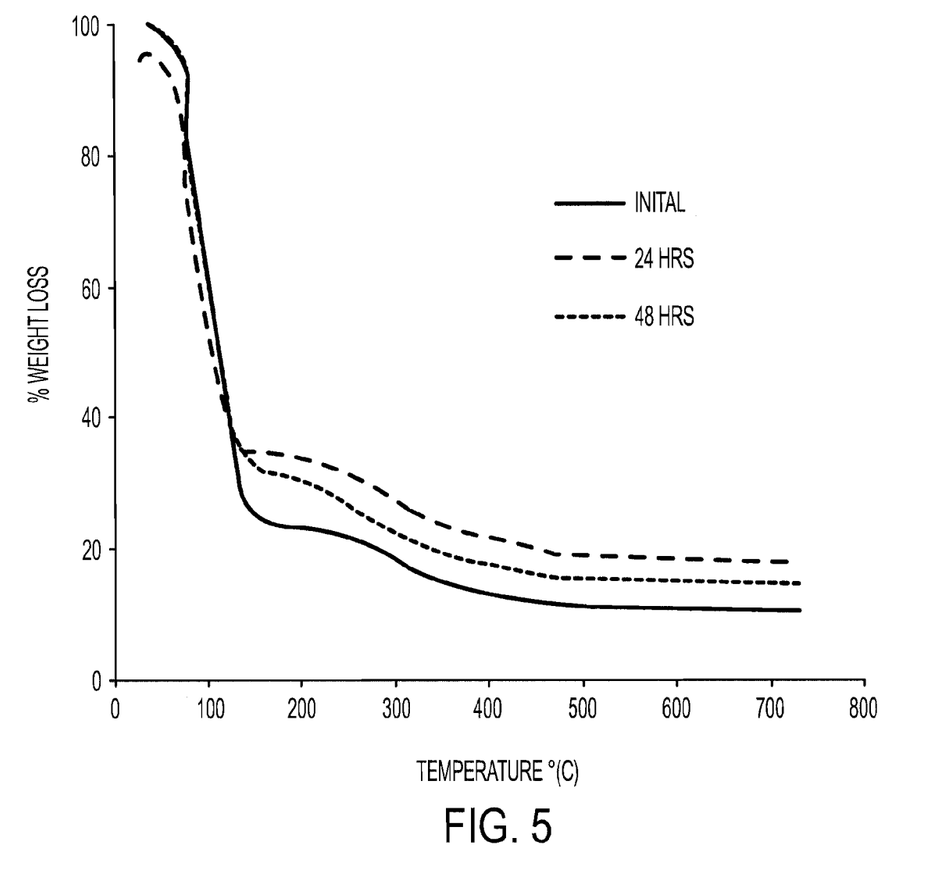
FIG. 5 shows time-dependent TGA chromatograms from the pyrolysis of swine waste with marine broth (control experiment).
Figure 6:
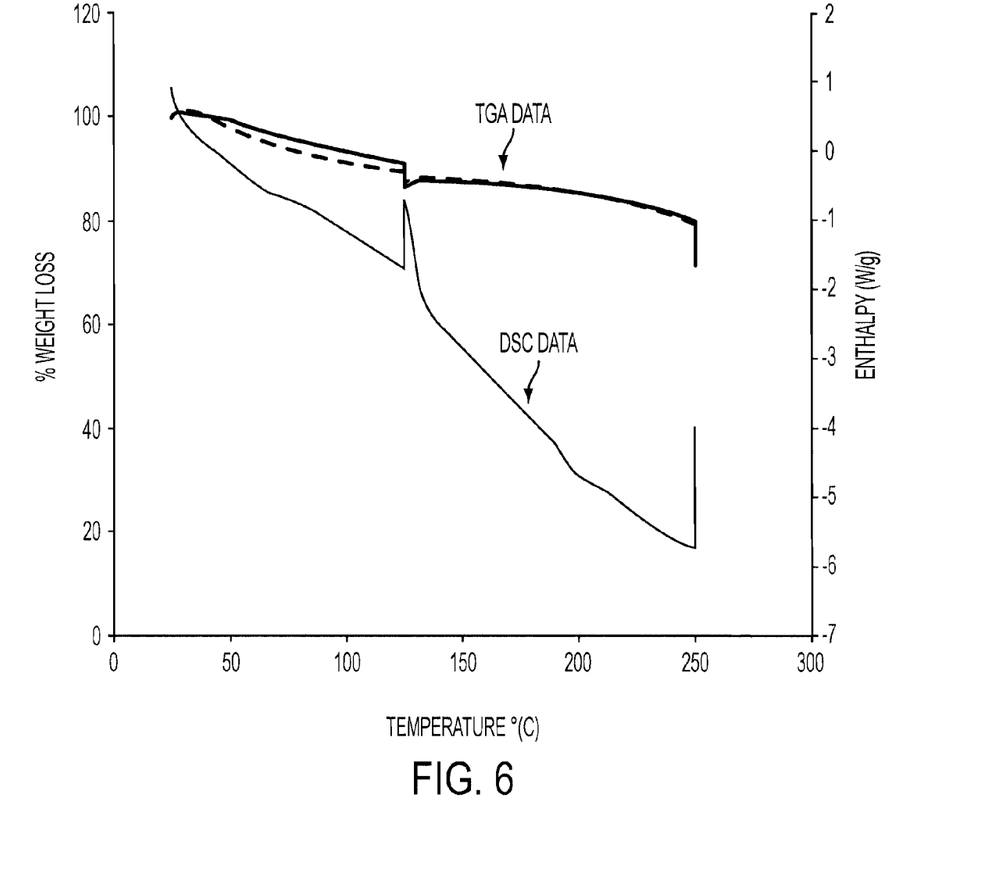
FIG. 6 shows a typical TGA/DSC data for waste enhanced samples pyrolysis for GC/FID.
Figure 7:
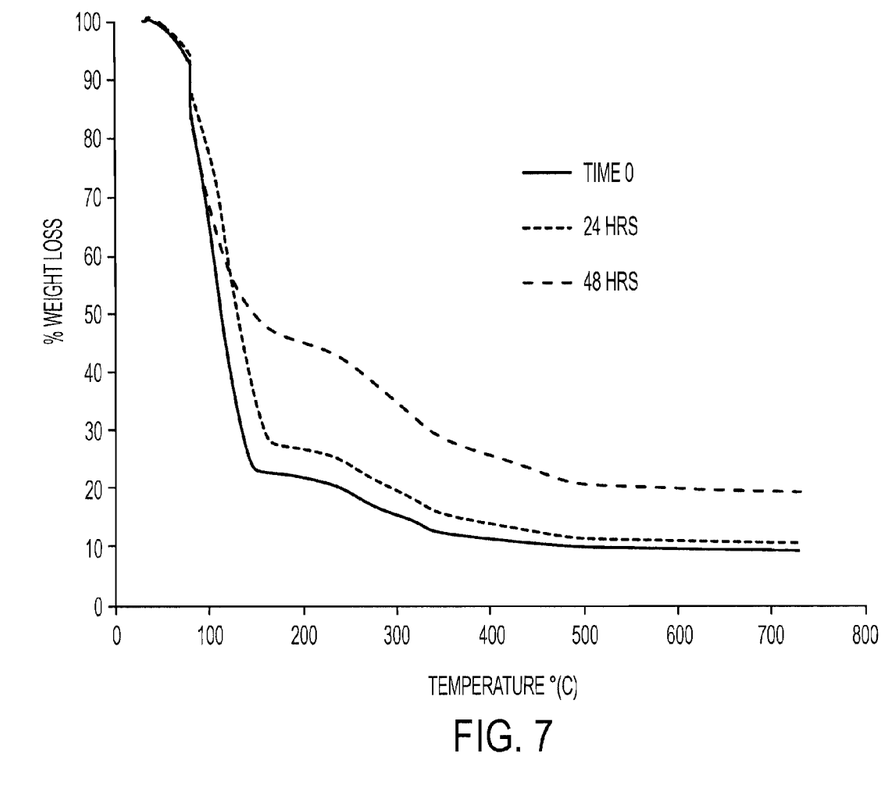
FIG. 7 shows time-dependent TGA chromatograms from the pyrolysis of *S. oneidensis* MR-1 with swine waste.
Figure 8:
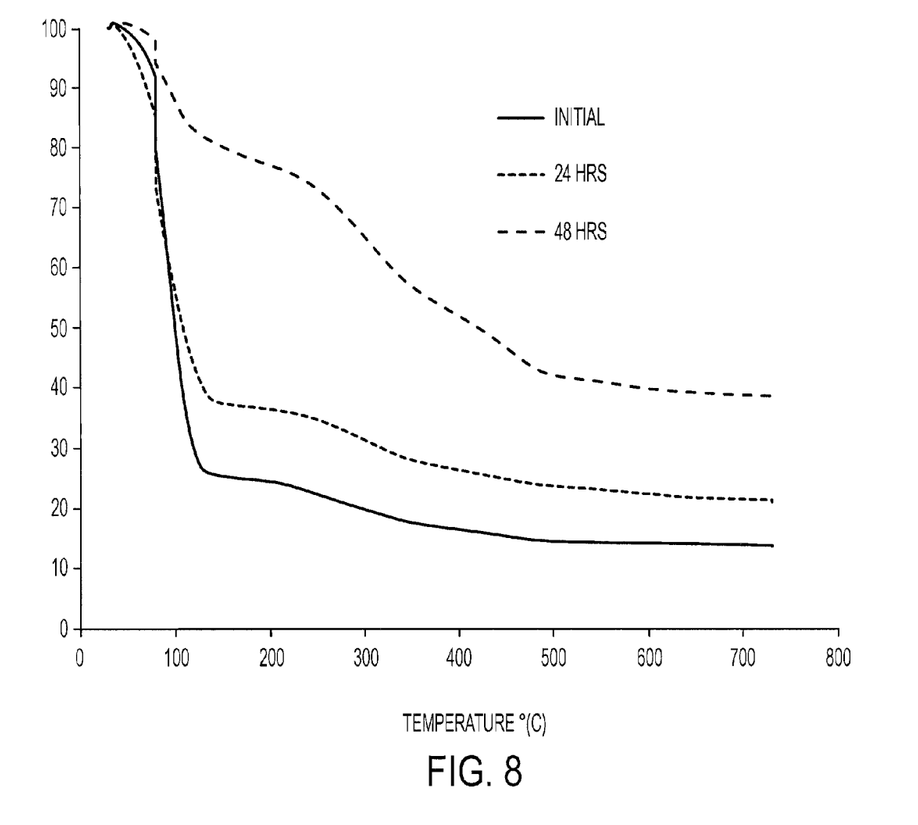
FIG. 8 time-dependent TGA chromatograms from the pyrolysis of *S. colwellianna* with swine waste.

Time-dependent treatment of defined waste streams with and without *Shewanella*—Full temperature scan TGA/DSC experiments (30-80° C. (20° C./min), 80° C. for 1 min, 80-730° C. (10° C./min), 730° C. for 5 min) were performed on both swine waste with and without *Shewanella* in 70 μL alumina crucibles. Samples were collected every 24 hours for over three days. A control experiment contained 50 mL swine waste with 50 mL of marine broth (FIG. 5). Experiments containing bacteria were created by mixing 50 mL swine waste with 50 mL of *S. oneidensis*, *S. oneidensis* MR-1, and *S. japonica* with cell concentrations between $2\text{-}5\times10^9$ CFU/mL. Each experiment was incubated at 25° C. with shaking (150 rpm). Each time point was centrifuged at 9000 g for 15 minutes and the sludge was dried in a vacuum oven (80° C. at 33 mm Hg) for 1 hour. Identical sample preparation was essential because of the sensitivity of the TGA analysis and residual water content creating variability in each spectrum. Differential scanning calorimetry (DSC) data has also been collected during each TGA scan to measure the specific heat released during phase transitions. DSC provides the ability to determine the heat released during pyrolysis between samples to define the amount of energy in the sludge samples. A typical DSC scan is provided in FIG. 6. FIGS. 5 and 7-9 show the control experiment, waste treated with *S. colwellianna*, waste treated with *S. japonica*, and waste treated with *S. oneidensis* MR-1, respectively. Pyrolysis occurs in each spectrum between 120-450° C. Integration of the percentage weight loss from each spectrum demonstrates an general increase in pyrolysis oils to greater than 9% for *S. colwellianna*. Without the introduction of *Shewanella*, there was no clear enhancement of the pyrolytic fraction as shown from the control experiment (FIG. 5) compared to all samples containing *Shewanella*.

EXAMPLE 5

Figure 9:
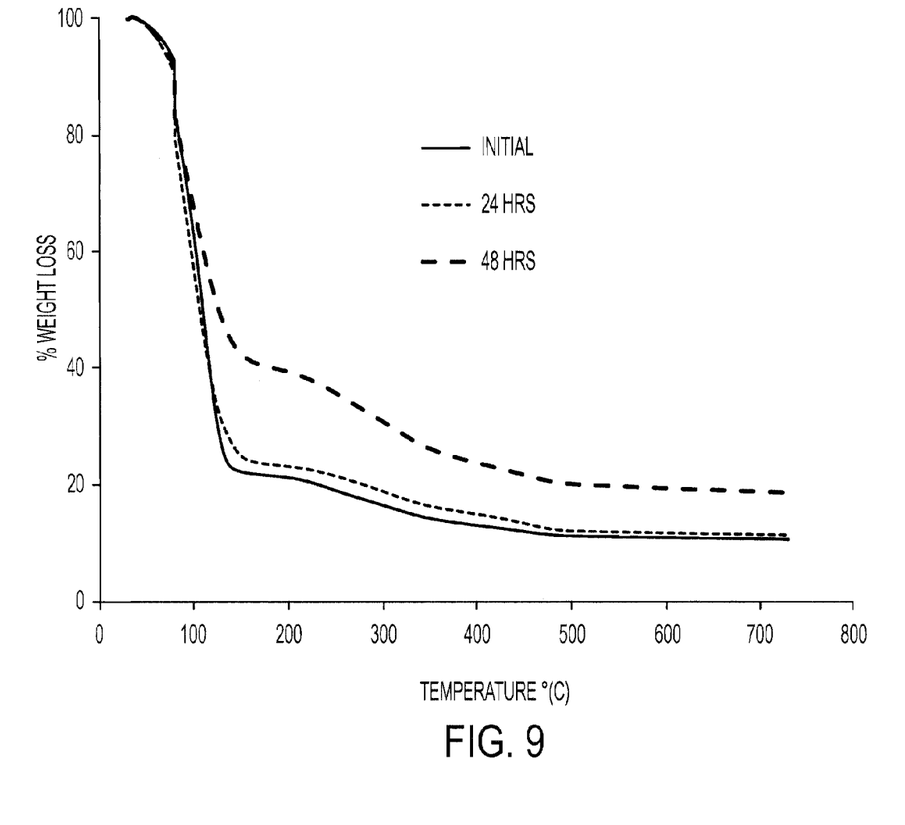
FIG. 9 time-dependent TGA chromatograms from the pyrolysis of *S. japonica* with swine waste.
Figure 10:
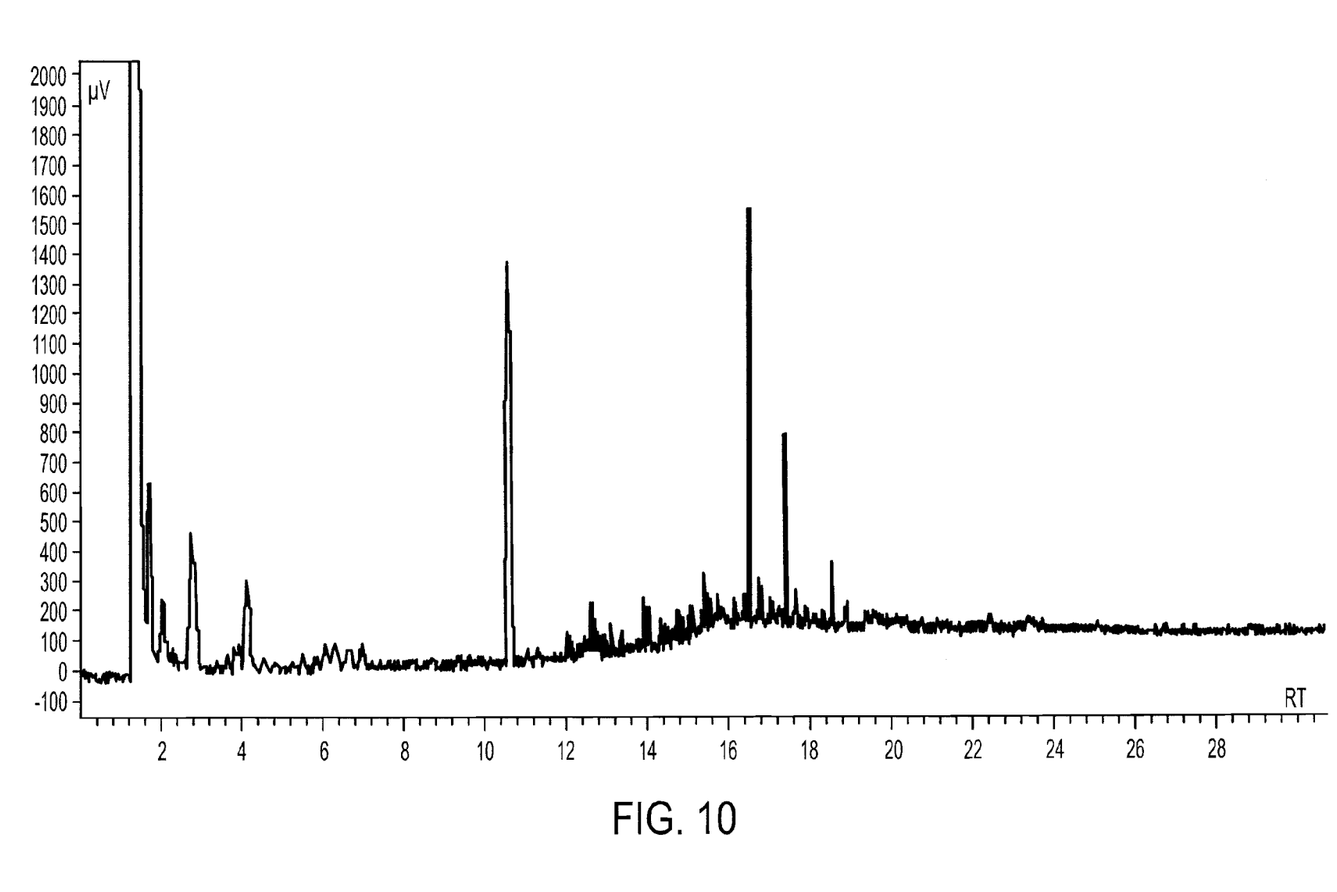
FIG. 10 shows a gas chromatograph of oil fraction after pyrolysis of swine waste.

Method for pyrolysis of defined waste streams for oil extraction—Waste samples (with and without *Shewanella*) were centrifuged at 9000 g for 15 minutes. The resulting sludge was placed into a 3 mL glass vial which was heated at 90° C. for 30 minutes to drive off residual water. Each sample was then placed in a 70 μL aluminum crucible. Each sample was then pyrolyzed within the TGA via a custom method (25-125° C. (10° C./min), 125° C. for 10 min, 125-250° C. (20° C./min), and 250° C. for 8 min) that maintains a temperature below 250° C. for 10 minutes (FIG. 9). Staying below 250° C. is necessary because of the large loss of oils noticeable from full temperature scan TGA experiments above this temperature (FIG. 4). Once the pyrolysis experiment was completed, the crucible was extracted into a water/dichloromethane solvent mixture. The mixture was then sonicated for 5 minutes and the isolated organic layer was dried over sodium sulfate. These extracts were then injected (1:8 split) onto a FAME capillary column within a Varian 450 gas chromatograph with flame ionization detector. FIG. 10 shows a typical chromatograph from the organic extract after the pyrolysis of swine waste with no microbial pre-treatment.

Figure 11:
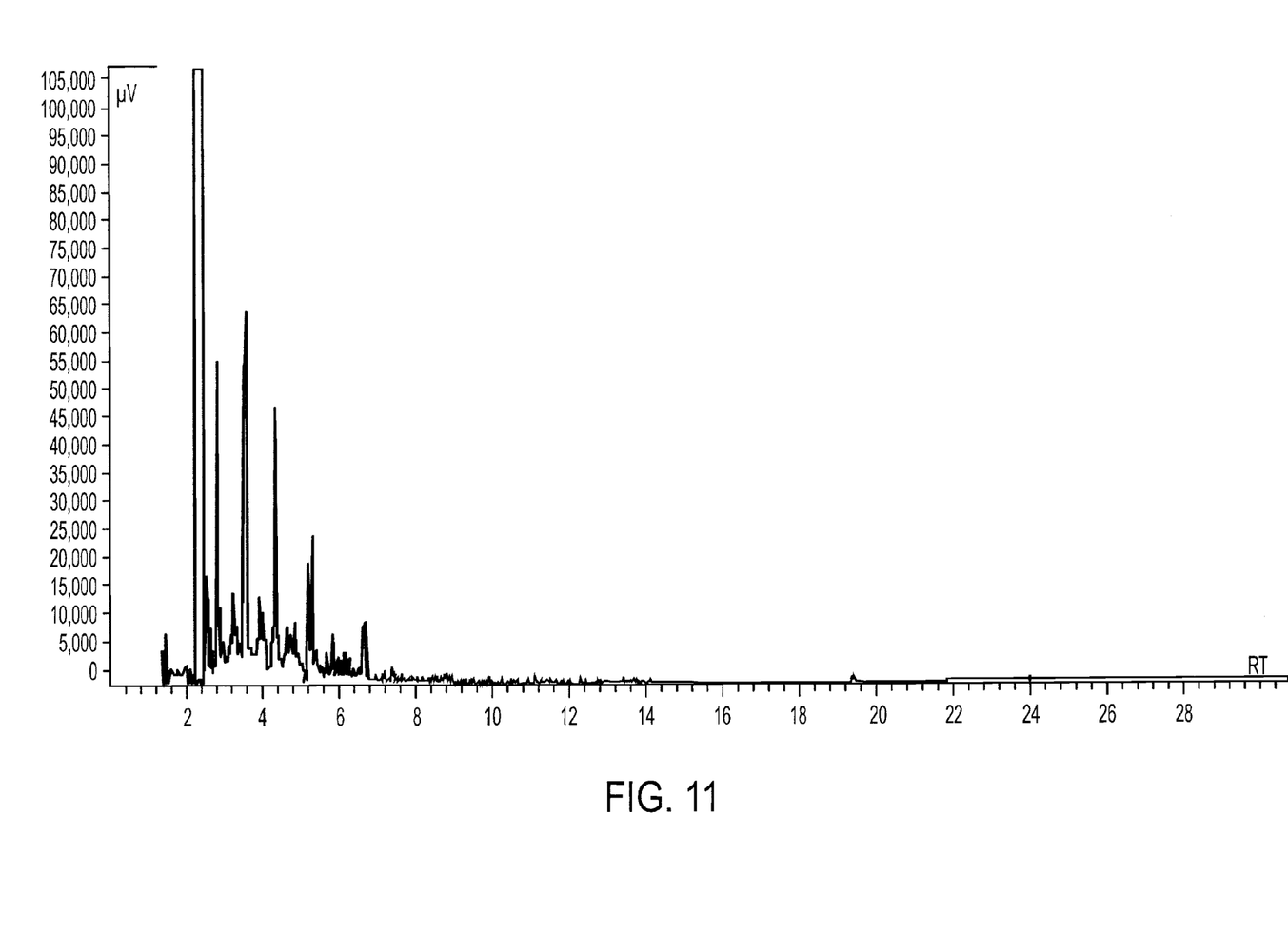
FIG. 11 shows a gas chromatograph of oil fraction after pyrolysis of swine waste with *S. colwellianna*.

A battery of alkane standards have been analyzed via the same GC method to describe where certain alkanes occur within the chromatograph. Table 1 defines the regions of interest for the alkanes desired. Comparison between FIGS. 10 and 11 shows that the amount of paraffin compounds generated from the pyrolysis of swine waste without bacterial modification to waste treated with *S. colwellianna* were significantly increased in both complexity and composition. These preliminary results indicate that alkanes between $C_6$-$C_{14}$ were enhanced in the presence of *S. colwellianna*. In general, all three *Shewanella* strains increase the amount of alkane and alkene components with *S. colwellianna* providing the largest percentage increase (9.2%).

TABLE 1

| General $C_4$-$C_{20}$ alkane retention times on FAME column in GC/FID | |
|---|---|
| Carbon chain length | Retention time range (min) |
| $C_4$-$C_9$ | 0.4-3.2 |
| $C_{10}$-$C_{15}$ | 3.3-11.1 |
| $C_{16}$-$C_{20}$ | 11.1-16.0 |

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A method comprising:
   providing a mixture comprising fecal waste and a bacterium;
      wherein the bacterium is a type that produces a $C_5$-$C_{32}$ fatty acid in the presence of any microbes in the fecal waste;
   incubating the mixture to produce a fatty acid enriched mixture;
   removing water from the fatty acid enriched mixture to produce a dried mixture; and
   pyrolyzing the dried mixture in an inert atmosphere to produce an alkane from the $C_5$-$C_{32}$ fatty acid.

2. The method of claim 1, wherein the bacterium is an environmental bacterium.

3. The method of claim 1, wherein the bacterium is *Shewanella japonica*.

4. The method of claim 1, wherein the bacterium is *Shewanella colwellianna*.

5. The method of claim 1, wherein the bacterium is *Shewanella oneidensis*.

6. The method of claim 1, wherein the bacterium is a spontaneous genetic mutant of a wild type bacterium.

7. The method of claim 1, wherein the bacterium is an environmentally conditioned strain of a wild type bacterium.

8. The method of claim 1, wherein the bacterium is a genetically engineered mutant of a wild type bacterium.

9. The method of claim 1, wherein the fecal waste is human fecal waste.

10. The method of claim 1, wherein the fecal waste is swine fecal waste.

11. The method of claim 1, wherein the pyrolysis is by a furnace.

12. The method of claim 1, wherein the pyrolysis is by microwave irradiation.

13. The method of claim 1, further comprising:
    collecting the water removed from the fatty acid enriched mixture.

14. The method of claim 1, further comprising:
    extracting the alkane from the pyrolized mixture.

15. The method of claim 1, wherein the pyrolysis is performed at 120-450° C.

16. The method of claim 1, wherein the pyrolysis is performed from 125° C. to less than 250° C.

17. The method of claim 1, wherein the bacterium is a *Shewanella* sp.

* * * * *